(12) United States Patent
Reid et al.

(10) Patent No.: US 7,829,855 B2
(45) Date of Patent: Nov. 9, 2010

(54) METHODS AND APPARATUS FOR DETERMINING FIBRE ORIENTATION

(75) Inventors: Matthew E. Reid, Prince George (CA); Robert Fedosejevs, Edmonton (CA)

(73) Assignee: University of Northern British Columbia, Prince George (CA)

( * ) Notice: Subject to any disclaimer, the term of this patent is extended or adjusted under 35 U.S.C. 154(b) by 120 days.

(21) Appl. No.: 12/161,292

(22) PCT Filed: Jan. 17, 2007

(86) PCT No.: PCT/CA2007/000062

§ 371 (c)(1), (2), (4) Date: Feb. 12, 2009

(87) PCT Pub. No.: WO2007/082371

PCT Pub. Date: Jul. 26, 2007

(65) Prior Publication Data

US 2010/0219343 A1      Sep. 2, 2010

Related U.S. Application Data

(60) Provisional application No. 60/759,042, filed on Jan. 17, 2006.

(51) Int. Cl.
*G01J 5/58*     (2006.01)
(52) U.S. Cl. .................... 250/341.3; 356/429
(58) Field of Classification Search ............ 250/341.1, 250/341.3; 162/131, 198, 263; 356/429
See application file for complete search history.

(56) References Cited

U.S. PATENT DOCUMENTS

| | | | |
|---|---|---|---|
| 4,648,712 A * | 3/1987 | Brenholdt | ............... 356/73 |
| 4,654,529 A | 3/1987 | Boulay et al. | |
| 4,707,652 A | 11/1987 | Lowitz | |
| 5,319,194 A | 6/1994 | Yoshizumi et al. | |
| 5,420,595 A | 5/1995 | Zhang et al. | |
| 5,475,233 A * | 12/1995 | Fukuoka et al. | .......... 250/559.1 |
| 5,619,143 A | 4/1997 | Stevens et al. | |
| 6,190,153 B1 * | 2/2001 | Tsuzukiyama et al. | ...... 425/135 |

(Continued)

FOREIGN PATENT DOCUMENTS

GB      2360842 B1      10/2001

(Continued)

OTHER PUBLICATIONS

Friedlander, P.H., "The measurement of fibre orientation in newsprint with respect to the machine direction by X-ray diffraction", Pulp and Paper Magazine of Canada, Jan. 1958, pp. 102-103.

(Continued)

*Primary Examiner*—David P Porta
*Assistant Examiner*—Marcus H Taningco
(74) *Attorney, Agent, or Firm*—Oyen Wiggs Green & Mutala LLP

(57) ABSTRACT

Fiber distribution characteristics such as the bulk average orientation of fibers in composite fibrous materials can be evaluated based on the variation in the speed with which polarized electromagnetic signals propagate through the material as a function of angle. The electromagnetic radiation may comprise terahertz radiation. The composite fibrous materials may be wood-containing materials such as oriented strand board or particle board.

26 Claims, 8 Drawing Sheets

U.S. PATENT DOCUMENTS

| | | | |
|---|---|---|---|
| 6,717,675 B1 * | 4/2004 | Munch | 356/429 |
| 2003/0156293 A1 * | 8/2003 | Kazuhiko et al. | 356/446 |
| 2003/0174312 A1 * | 9/2003 | Leblanc | 356/73.1 |
| 2004/0155665 A1 | 8/2004 | Arnone et al. | |
| 2005/0253071 A1 | 11/2005 | Ferguson et al. | |

FOREIGN PATENT DOCUMENTS

| | | |
|---|---|---|
| GB | 2410081 A1 | 7/2005 |
| WO | 86/07148 A1 | 12/1986 |

OTHER PUBLICATIONS

Ruck, H. et al., "The determination of the fibre orientation in paper", Plup and Paper Magazine of Canada, Jun. 1958, pp. 183-190.

Zhao, G. et al., "Design and performance of THz emission and detection setup based on a semi-insulating GaAs emitter", Rev. Sci. Inst. vol. 73, pp. 1715-1719.

* cited by examiner

METHODS AND APPARATUS FOR DETERMINING FIBRE ORIENTATION

CROSS-REFERENCE TO RELATED APPLICATION

This application claims priority from U.S. patent application No. 60/759,042 filed on 17 Jan. 2006 and entitled METHODS AND APPARATUS FOR DETERMINING FIBRE ORIENTATION. For purposes of the United States of America, this application claims the benefit under 35 U.S.C.§119 of U.S. patent application No. 60/759,042 filed on 17 Jan. 2006 and entitled METHODS AND APPARATUS FOR DETERMINING FIBRE ORIENTATION which is hereby incorporated herein by reference.

TECHNICAL FIELD

The invention relates to methods for determining the orientations of fibers and/or the degree of anisotropy in the orientations of fibers in products made from fibrous materials. The invention has application, for example, in determining the orientations of wood fibers in materials made from wood.

BACKGROUND

Engineered wood products such as oriented strand board (OSB) and particle board are made by adhering together fragments of wood. The properties of the resulting materials depend significantly upon the way in which the fragments are aligned with one another as well as the orientations of fibers within the fragments of wood.

The strength properties of many composite fibrous materials are sub-optimal in cases where fibers in the materials are arranged so that the fibers are preferentially aligned in one direction. For example, in OSB, if adjacent layers of wood chips are not aligned with grain extending perpendicularly to one another then the mechanical strength of the OSB will be reduced. Similarly, the orientation of fibers in paper can affect mechanical characteristics of the paper. In making composite fibrous products such as OSB or paper it would be desirable to have a way to evaluate whether fibers in the products are arranged optimally or not.

There are various ways to measure fiber orientations. Some of these are as follows:

One can dissect samples of a material under a microscope. This is not a practical method for process control.

One can measure DC or low-frequency AC dielectric constants of the material. The dielectric constant perpendicular to the wood grain is known to be different from the dielectric constant parallel to the wood grain. It is not practical to use measurements of dielectric constant for process control because measuring the dielectric constant of a material is typically too slow and also requires contact with the material in most cases.

Optical methods can be used to determine fiber orientation but these methods can only determine the orientation of fibers at the surface of the material.

X-ray analysis may be performed, however the equipment required for X-ray analysis is expensive and there are safety issues with X-rays. P. H. Friedlander "The measurement of fiber orientation in newsprint with respect to the machine direction by X-ray diffraction" Pulp and Paper Magazine of Canada, June 1958, pp. 102-103 and H. Ruck et al., "The determination of the fiber orientation in paper" Pulp and Paper Magazine of Canada, June 1958, pp. 183-190 disclose the use of X-ray diffraction to monitor fiber orientation in paper.

U.S. Pat. No. 4,654,529 entitled "Method for measuring the fiber orientation anisotropy in a fibrous structure" discloses a method for evaluating the fiber alignment anisotropy in a fibrous structure by measuring attenuation as a function of polarization There is a need for technology that can be used to determine fiber orientation and/or the degree of anisotropy in fiber orientation in composite fibrous materials. There is a particular need for such technology that can be applied in industrial settings.

SUMMARY OF THE INVENTION

This invention provides methods and apparatus for characterizing the arrangement of fibers in a composite fibrous material. Some non-limiting examples of composite fibrous materials are OSB, particle board, paper, cardboard, fiberglass, carbon fiber composites and solid wood.

One aspect of the invention provides methods for measuring average orientations of fibers in a composite fibrous material. The methods comprise passing first electromagnetic radiation through the material, the first electromagnetic radiation having a first polarization state and passing second electromagnetic radiation through the material, the second electromagnetic radiation having a second polarization state. The first and second electromagnetic radiation have one or more wavelengths at which the material is not opaque. The first and second radiation may comprise electromagnetic pulses having terahertz frequencies. The methods comprise detecting the first and second electromagnetic radiation that has passed though the material and, obtaining a measure of birefringence of the sample at the wavelengths of the electromagnetic radiation. The measure of birefringence is based at least in part on the detected first and second electromagnetic radiation.

Another aspect of the invention provides a method for determining the degree to which the fibers in a composite fibrous material are oriented in a preferred direction. The method comprises measuring an angular dependance of a speed of propagation of polarized electromagnetic radiation in the material by passing the electromagnetic radiation through the material. The electromagnetic radiation is polarized along a polarization axis. The polarization axis is parallel to a plane of the material and makes an angle with a reference axis in the plane of the material. The electromagnetic radiation has one or more wavelengths at which the material is not opaque and at which the material exhibits birefringence. The electromagnetic radiation may comprise terahertz (THz) radiation. In some embodiments the method comprises changing the angle and repeating measuring the speed of propagation of the electromagnetic radiation in the material, and monitoring variation of the speed of propagation as a function of the angle. In some embodiments, a volume-averaged fiber orientation is determined based on the variation of the speed of propagation as a function of the angle.

The speed of propagation of the electromagnetic radiation may be measured directly at different angles. In the alternative, variations in the speed of propagation with polarization angle may be measured indirectly, for example, by observing a change in polarization caused by interaction between the electromagnetic radiation and the material.

Another aspect of the invention provides apparatus for quality control in the manufacture of a composite fibrous material. The apparatus comprises a source of THz radiation, a detector of THz radiation and a controller. The source of THz radiation is located to direct polarized THz radiation at a first face of a moving web of the composite fibrous material. The THz radiation has a selected polarization state. Where the THz radiation is linearly polarized, a polarization axis of the THz radiation makes an angle with a direction of motion of the web. The detector of THz radiation is located to receive the THz radiation originating from the source and emerging on a second face of the composite fibrous material. The controller is connected to control the angle and is configured to operate the detector and to obtain a measure of birefringence of the material at wavelengths of the THz radiation. The birefringence measure may be based on speeds of the THz radiation in the material (or, equivalently, a measure of the index of refraction of the material at THz frequencies) for each of a plurality of polarization states.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention will be described in the context of a stand-alone instrument for use in the inspection and failure analysis of multi-layered wood structures and an on-line monitor for determining the orientation of wood fibers in wood chips or boards in a plant for making particle board or OSB. The invention is not limited to these applications. The apparatus and methods disclosed herein may be extended to:

the analysis of fiber orientations in materials made from fibers originating from starting materials other than wood, such as fiberglass, carbon fiber composites;

the analysis of wood grain direction and structure in solid wood; and, process control in the manufacture of products other than boards (for example, process control in making paper and other fiber-based products).

Figure 1:
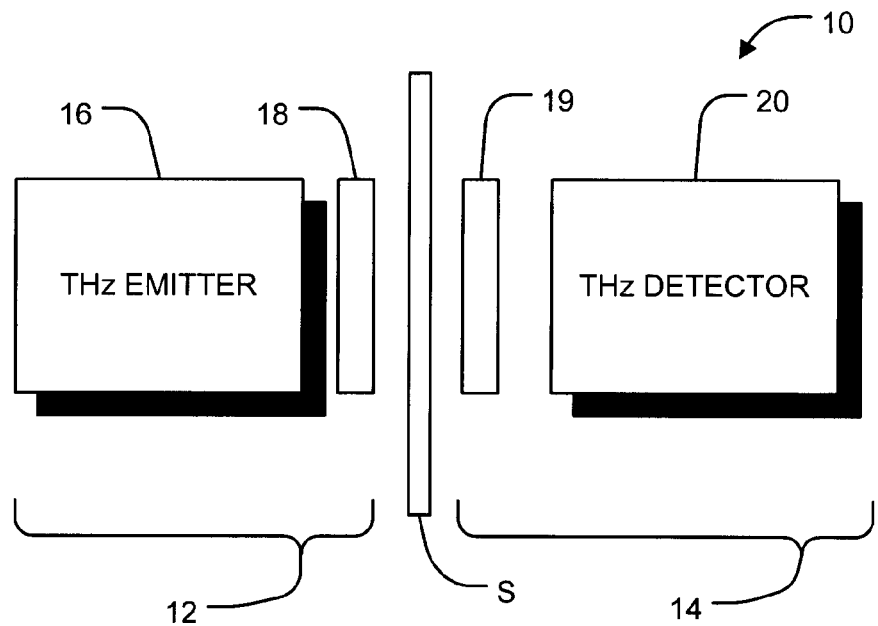
FIG. 1 is a block diagram of apparatus for measuring the bulk average fiber orientation in a sample of a material.

FIG. 1 shows a stand-alone apparatus 10 for determining bulk average fiber orientation in a sample of material. In this example, the sample of material is a piece of wood. Apparatus 10 exploits the fact that wood is essentially transparent to electromagnetic radiation in a broad frequency range extending up to the terahertz (THz) region of the spectrum and that wood is birefringent in this frequency range (i.e. the propagation speed of a polarized THz signal through wood depends upon the direction of polarization of the signal relative to the direction of the grain of the wood through which the signal is propagating). The term "THz radiation" as used herein means radiation having frequencies in the range of 0.01 to 3 THz. Frequencies in the range of 0.2 to 1.4 THz are particularly useful for studying fiber orientation in wood products.

Apparatus 10 comprises a source 12 of polarized THz radiation on one side of a sample S and an analyser 14 on an opposite side of sample S. Polarized THz radiation from source 12 passes through sample S and is detected at analyser 14. Analyzer 14 detects directly or indirectly the average speed of propagation of the THz radiation as it passes through the sample (or, equivalently, the degree to which the sample delays the THz radiation).

In the illustrated embodiment, source 12 comprises an emitter 16 and a polarizer 18. Emitter 16 emits very short pulses of radiation (for example, pulses on the order of 0.5 ps in duration). Such pulses have a bandwidth on the order of 1 THz.

Analyser 14 comprises a polarizer 19 and a detector 20. Polarizers 18 and 19 can be set to a desired angle with respect to sample S. When source 12 emits a THz pulse, the pulse is detected by detector 20. The time elapsed between the emission and detection of the pulse can be determined. This can be repeated at different angular settings of polarizers 18 and 19 relative to sample S.

Apparatus 10 may be used to evaluate the degree to which a sample S consisting of a solid piece of wood exhibits birefringence. Apparatus 10 can also be applied to evaluate the degree to which the fibers are aligned in a preferred direction in a sample of a material made of multiple smaller pieces or wood or other fibrous birefringent material.

Apparatus 10 may be used by first transmitting a reference pulse in the absence of sample S. The reference pulse provides an indication of incident power. The transmission spectra of the sample S can be determined by computing the ratio of transmitted power to incident power.

Figure 2:
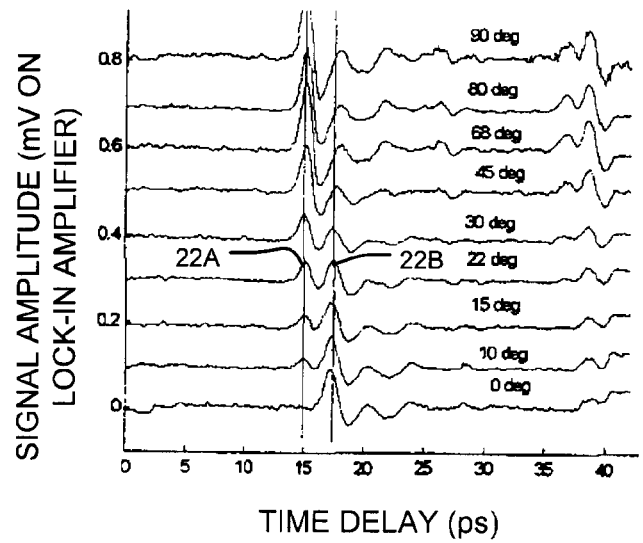
FIG. 2 shows plots of received signal as a function of time for various angles between the polarization axis of a THz signal and a wood sample.

If the ratio of the product of the thickness of sample S and the birefringence of sample S to the speed of light in vacuum is at least as great as the duration of the pulse emitted by source 12 then the birefringence of a sample S can be measured directly in the time domain. FIG. 2 shows plots of received signal as a function of time for various angles of polarizers 18 and 19 relative to the grain of a sample of poplar 6.54 mm thick. In FIG. 2, zero degrees corresponds to alignment of the axis of polarization with the grain of the sample and ninety degrees corresponds to the axis of polarization being perpendicular to the grain of the sample.

It can be seen in FIG. 2 that, at some angles, two time-separated pulses can be seen in the detected signal. For example, with the polarizers 18 and 19 set at an angle of 22 degrees to the grain of sample S, a first pulse 22A is detected at a time delay of approximately 15 ps and a second pulse 22B is detected at a time delay of approximately 17½ ps.

An estimate of the frequency-averaged birefringence Δn of sample S can be obtained directly from this time domain data. If Δτ is the difference in time between pulses 22A and 22B then Δn is given by:

$$\Delta n = \frac{c\Delta\tau}{L} \quad (1)$$

where L is the thickness of sample S.

Another way to obtain a measure of the birefringence of sample S is to obtain a measure of the index of refraction of sample S. Where detection is coherent, the frequency-resolved, complex, index of refraction can be determined directly from the measured data. The ratio of the strength of the transmitted signal to the incident signal as a function of frequency can be approximated for a thick sample by:

$$\frac{\vec{E}_{SAMPLE}(v)}{\vec{E}_{REF}(v)} = \hat{t}_{AW}\hat{t}_{WA} e^{-\frac{i2\pi vL}{c}(\hat{n}_W - \hat{n}_A)} = \text{Re}^{i\theta} \quad (2)$$

where:

$\vec{E}_{SAMPLE}(v)$ is the field strength of the component of the transmitted signal at the frequency v;

$\vec{E}_{REF}(v)$ is the field strength of the component of the incident signal at the frequency v;

c is the speed of light in vacuum;

L is the thickness of the sample;

$\hat{t}_{AW}$ and $\hat{t}_{WA}$ are respectively the Fresnel transmission coefficients of an air-to-sample and sample-to-air interface; and, $\hat{n}_W$ and $\hat{n}_A$ are the complex indices of refraction in the sample and in air respectively and $\hat{n}_A=1$.

Since:

$$\hat{n}_W = n_W - ik_W \quad (3)$$

where k is the dielectric constant of the sample it can be shown that:

$$n_W = -\frac{\theta c}{2\pi vL} + 1 \quad (4)$$

and also that:

$$a_W = -\frac{2}{L}\ln\left(R\frac{(n_W+1)^2}{4n_w}\right) \quad (5)$$

where $\alpha_W$ is the absorption coefficient of the sample. Equations (4) and (5) are based on the assumption that k<<n. For more general values of k, the values of $n_w$ and $\alpha_w$ can be evaluated but the calculations are more complicated than these simple expressions.

Figure 3:
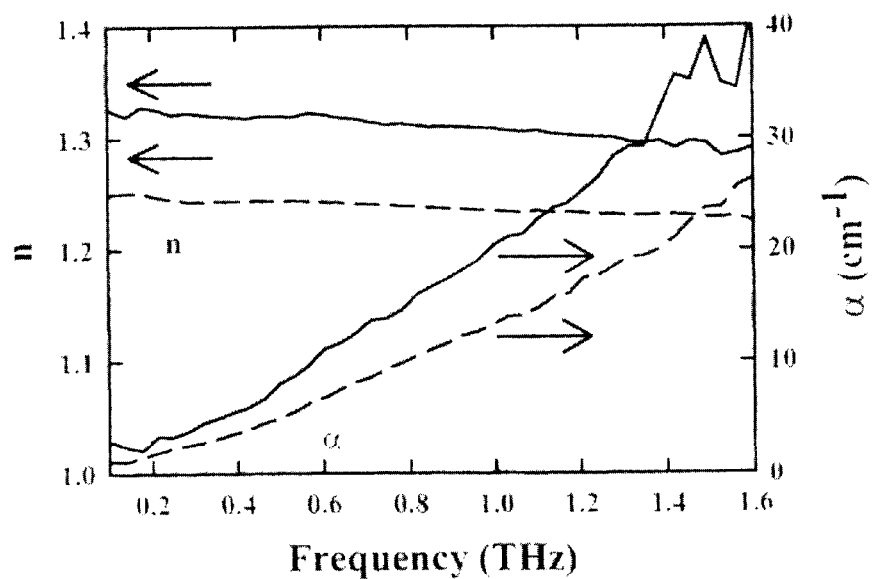
FIG. 3 shows results of measurements of index of refraction, $n_W$, and absorption coefficient, $\alpha_W$, as a function of frequency for a sample of spruce wood.

FIG. 3 shows measurements of $n_W$ and $\alpha_W$ as a function of frequency for a sample of spruce wood having a thickness of 3.025 mm. The values for $n_W$ and $\alpha_W$ presented in solid lines are based upon a reference signal received with no wood sample present and signals transmitted through the wood with the polarization parallel to the wood grain. The values for $n_W$ and $\alpha_W$ presented in dashed lines are based upon the reference signal and signals transmitted through the wood with the polarization perpendicular to the wood grain. It can be seen that both $n_W$ and $\alpha_W$ differ significantly for signals polarized parallel to the grain and for signals polarized perpendicular to the grain of the wood sample.

Since $n_W$ varies with the angle between the direction of the grain of a sample and the direction of polarization of the signal, and $n_W$ is related to the speed at which the signal propagates through the sample, one can obtain a measure of the degree to which fibers in the sample extend preferentially in some direction (i.e. the degree of anisotropy of the arrangement of fibers in the sample) by monitoring the time taken for signals to propagate through the sample as the angle of polarization of the signal relative to the sample is varied.

Figure 4:
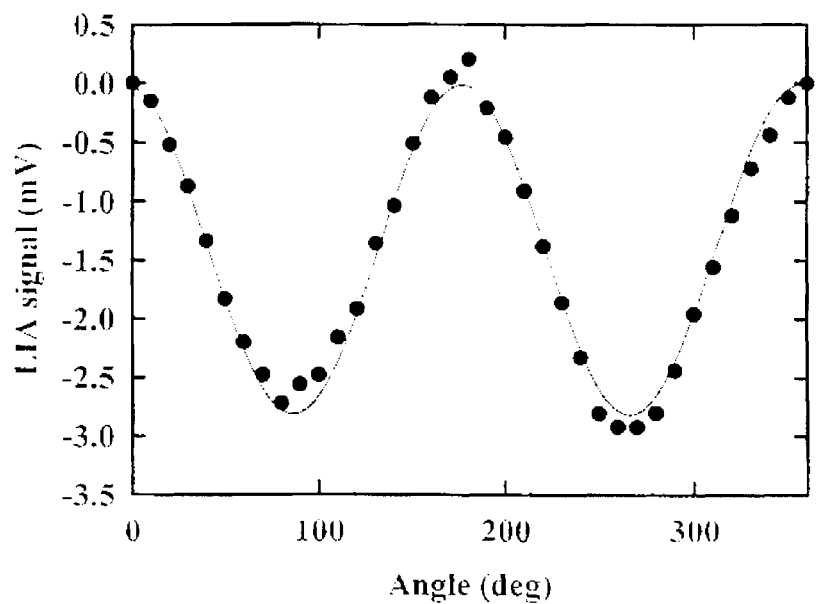
FIG. 4 illustrates variations in the time taken for a THz signal to propagate through a sample as a function of angle, the sample is made up of 27 sheets of lens paper stacked so that the directions in which fibers in each sheet are preferentially oriented are aligned.

FIG. 4 illustrates variations in the time taken for a THz signal to propagate through a sample made up of 27 sheets of lens paper stacked so that the directions in which fibers are preferentially oriented in each sheet are aligned. The signal was polarized in the horizontal direction (i.e. at an angle of 90 degrees) while the sample was rotated. It can be seen that there is a significant variation in the signal as a function of angle. It can also be seen that all of the information in the plot of FIG. 4 can be obtained by scanning the angle through 90 degrees.

Figure 5:
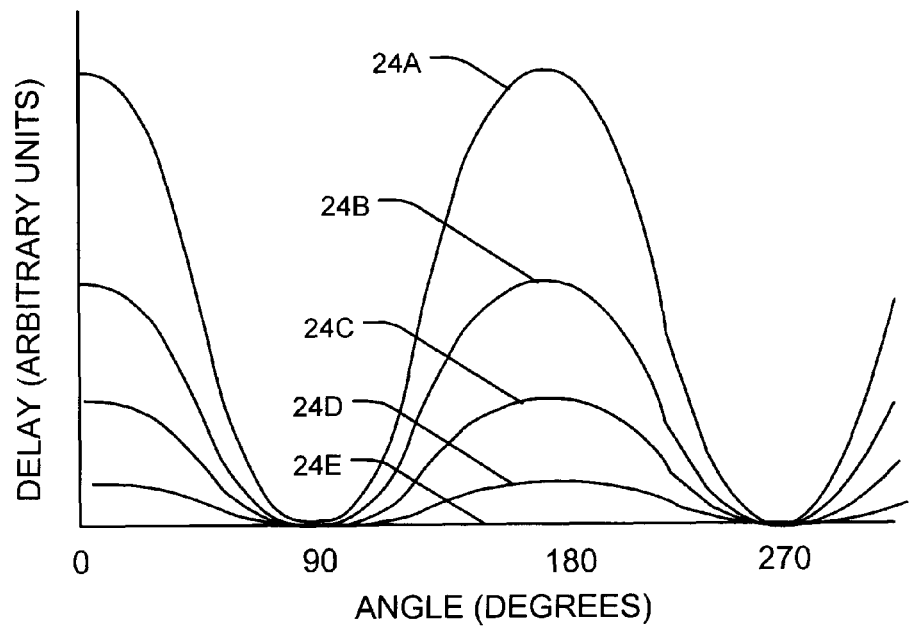
FIG. 5 is a set of plots illustrating the expected variation in the time taken for a THz signal to propagate through samples in which fibers are oriented with differing degrees of anisotropy.

In the examples above, the samples for which data has been presented have been samples of solid wood having the grain running in a direction perpendicular to the direction of propagation of the signal. Consider the case where the signal passes through different regions in which the grain runs in different directions. In such cases the signal will propagate through the sample in a time that depends upon the thicknesses of the different regions and on the orientations of the grain in the different regions relative to a direction of polarization of the signal. If there are a lot of different regions and the grain directions of the different regions are random then there will be no preferred grain direction and the time taken for the signals to propagate through the sample will not vary significantly as the direction of polarization of the signals is rotated relative to the sample. On the other hand, if there is one preferred grain direction then the signal propagation time will vary in the general manner shown in curve 24A of FIG. 5. If there are two or more preferred grain directions (as, for example, in the case where, in some regions, the grain is oriented in a first direction and in other regions the grain is oriented in a second direction perpendicular to the first direction) but, on average, the fibers are still oriented in a preferred direction then one would expect the signal propagation time to vary by a smaller amount, as indicated by curves 24B, 24C and 24D of FIG. 5. If, in the volume through which the radiation passes, the same number of fibers are oriented in each of the two directions then the signal propagation time will not vary significantly with angle, as indicated by line 24E.

One can obtain an indication of the degree to which fibers in the sample are aligned preferentially in one or more directions by obtaining a measure of how the signal propagation time varies for different angles between a direction of polarization of the signal and a sample. The speed of propagation may be measured directly or indirectly.

One way to make such measurements is through use of a THz detector capable of making time-resolved measurements of the time taken for a THz signal to pass through a sample.

Figure 6:
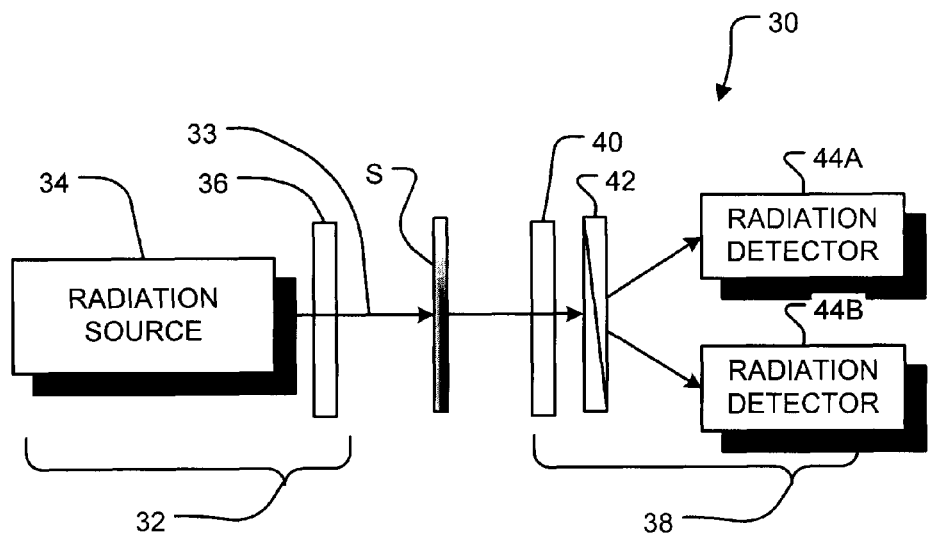
FIGS. 6, 6A, 7, and 7A are schematic views showing alternative apparatus for evaluating the degree to which the transmission time of a polarized signal varies with the angle of the polarization axis of the signal relative to a sample.

Various other apparatus may be used to evaluate the degree to which the transmission time of a polarized signal varies with angle. FIG. 6 shows one example apparatus 30. Apparatus 30 has a source 32 of polarized far-infrared radiation 33. In the illustrated example, source 32 comprises a continuous wave (cw) far-infrared laser 34 and a polarizer 36. Polarizer 36 may comprise a wire-grid polarizer, for example. Radiation 33 from source 32 passes through sample S to a detection system 38 comprising a quarter-wave plate 40, a polarizing beam splitter 42 and a pair of detectors 44A and 44B. Quarter-wave plate 40 is adjusted so that, in the absence of sample S, the signals detected at detectors 44A and 44B are equal.

If sample S exhibits birefringence, the polarization state of radiation 33 changes as radiation 33 passes through sample S. This change results in the signals at detectors 44A and 44B being different. The angle between the direction of polarization of incident radiation 33 and the grain orientation in sample S can be determined, for example, from the relationship:

$$\left(\frac{S_{44A} - S_{44B}}{S_{44A} + S_{44B}}\right) = \sin(2\theta)\sin[\Gamma] \quad (6)$$

where:
$S_{44A}$ and $S_{44B}$ are the signals output by detectors 44A and 44B respectively;
$\theta$ is the angle between the signal polarization direction and the grain of sample S; and,
$\Gamma$ is the phase retardation introduced by sample S.
$\Gamma$ depends both on the thickness of sample S and the magnitude of the birefringence of sample S at the wavelength of radiation 33.

Apparatus 30 may be used to determine the residual volume-averaged fiber orientation within a composite sample. Since Equation (6) has two unknowns ($\theta$ and $\Gamma$) it is necessary to obtain values of $S_{44A}$ and $S_{44B}$ for each of at least two different polarization states of the input signal to solve for both $\theta$ and $\Gamma$.

Consider, for example, the case where a first THz input signal is linearly polarized and has an axis of polarization that makes an unknown angle $\theta$ with a preferred axis of sample S. A second THz input signal is also linearly polarized but has an axis of polarization that makes an angle $\theta+\pi/4$ with the preferred axis of sample S. If the value of the left-hand side of Equation (6) is designated as a for the first THz input signal and as b for the second THz input signal then it can be shown that:

$$\theta = \frac{1}{2}\tan^{-1}\left(\frac{a}{b}\right) \quad (7)$$

and also that:

$$\Gamma = \sin^{-1}\left(\frac{a}{\sin(\tan^{-1}(a/b))}\right) = \sin^{-1}\left(\frac{a}{\sin(2\theta)}\right) \quad (8)$$

or, equivalently, $$\Gamma = \sin^{-1}\left(\frac{b}{\cos(\tan^{-1}(a/b))}\right) = \sin^{-1}\left(\frac{b}{\cos(2\theta)}\right) \quad (9)$$

Apparatus 30 of FIG. 6 may be used to obtain values for a and b. During the measurement of a, polarizer 36 and polarizing beam splitter 42 are oriented appropriately for the first THz input signal. During the measurement of b, polarizer 36 and polarizing beam splitter 42 are oriented appropriately for the second THz input signal. This can be achieved, for example, by rotating apparatus 30 relative to sample S about the optical axis of radiation 33 between measurements of the first and second signals.

Figure 6A:
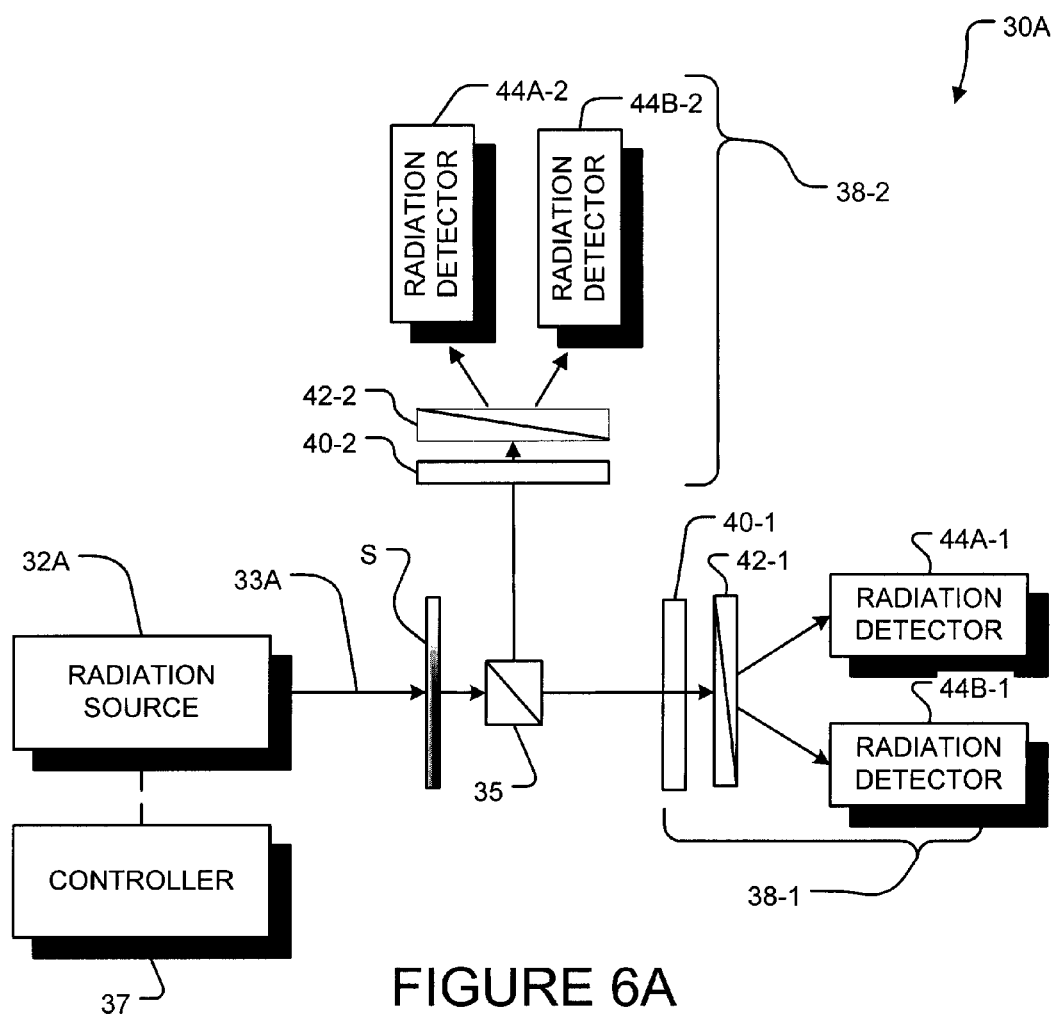

As noted above, a and b may be measured essentially simultaneously. FIG. 6A shows an apparatus 30A that can be used for this purpose. Apparatus 30A has a source 32A of polarized THz radiation 33A. Source 32A may be controlled to selectively generate THz radiation in one of at least two polarization states. For example, source 32A may generate THz radiation in one of a first polarization state L1 and a second polarization state L2. The first and second polarization states may be linear polarization states although, in general this is not necessary. One or both of the first and second polarization states could be a circular, elliptical, or other distinct polarization state. L1 and L2 are not necessarily orthogonal to one another. For example, where L1 and L2 are linear polarization states, the polarization vectors of L1 and L2 may be rotated through an angle in the range of 30 degrees to 60 degrees (e.g. approximately 45 degrees) relative to one another.

The THz radiation passes through sample S and is then separated into two parts, preferably equal parts. In apparatus 30A this is achieved by passing the radiation through a non-polarizing 50/50 beam splitter 35. Each part of the radiation is delivered to a detection system 38. Detector systems 38-1 and 38-2 are substantially similar to one another. A first detection system 38-1 comprises a quarter-wave plate 40-1, a polarizing beam splitter 42-1 and a pair of detectors 44A-1 and 44B-1. Polarizing beam splitter 42-1 is oriented to pass radiation of the first polarization state. A second detection system 38-2 comprises a quarter-wave plate 40-2, a polarizing beam splitter 42-2 and a pair of detectors 44A-2 and 44B-2. Polarizing beam splitter 42-2 is oriented to pass radiation of the second polarization state. Quarter-wave plate 40-1 is adjusted so that, in the absence of sample S the signals detected at detectors 44A-1 and 44B-1 are equal for the first polarization state. Quarter-wave plate 40-2 is adjusted so that, in the absence of sample S the signals detected at detectors 44A-2 and 44B-2 are equal for the second polarization state.

Apparatus 30A can be operated by causing radiation source 32A to issue radiation in the first polarization state during a first time interval t1. In interval t1 the outputs of detectors 44A-1 and 44B-1 are captured. A value for a can be determined from the captured values as described above. Radiation source 32B is then caused to issue radiation in the second polarization state during a second time interval t2. In interval t2 the outputs of detectors 44A-2 and 44B-2 are captured. A value for b can be determined from the captured values as described above.

One way to exploit the invention is to pass THz radiation of two polarization states through sample S, essentially simultaneously (i.e. within a time period short enough that the sample does not move significantly between passing the radiation of the different polarization states through the sample). After transmission, for each of the input polarization states, two orthogonal polarization states may be measured differentially. This may be done, for example, as outlined above in the discussion of FIG. 6, with polarizing beam splitter 42 oriented differently for each of the input polarizations. The information so obtained may be used to extract information about both the preferred fiber-orientation direction and the magnitude of the birefringence of the sample.

To illustrate this, consider the case where the two input polarizations are linear and are not perpendicular to one another. For simplicity, consider the case where:

the first input polarization makes an arbitrary angle, θ, with a preferred axis along which fibers in the sample are preferentially oriented; and, the second input polarization makes an angle (θ+π/4) with the preferred axis.

Consider the case where the differential output of apparatus 30 (i.e. the left-hand side of Equation (6) above) has a value a for the first input polarization and has a value b for the second input polarization. It can be shown that:

$$\frac{1}{2}\tan^{-1}\left(\frac{a}{b}\right) = \theta \quad (10)$$

and also that the birefringence, Γ, is given by:

$$\Gamma = \sin^{-1}\left(\frac{a}{\sin(\tan^{-1}(a/b))}\right) \quad (11)$$

and also by:

$$\Gamma = \sin^{-1}\left(\frac{b}{\cos(\tan^{-1}(a/b))}\right) \quad (12)$$

In an industrial setting where it is desired to make measurements quickly, it may be desirable to make measurements essentially simultaneously for both input polarizations. This may be done in a number of ways including through use of an apparatus 30A as shown in FIG. 6A. Controller 37 causes source 32A to produce THz radiation having a first polarization state L1 for a first time period t1 and a second polarization state L2 for a second time period t2. L1 and L2 are not orthogonal to one another. The radiation is incident on and passes through sample S.

During time interval t1 the output of detectors 44A-1 and 44B-1 of detector assembly 38-1 are monitored and used to provide a value for the differential output a. During time interval t2 the output of detectors 44A-2 and 44B-2 of detector assembly 38-2 are monitored and used to provide a value for the differential output b. These differential output values can then be used to determine θ and Γ through the use of equation (7) and one of equations (8) and (9), for example.

Figure 7:
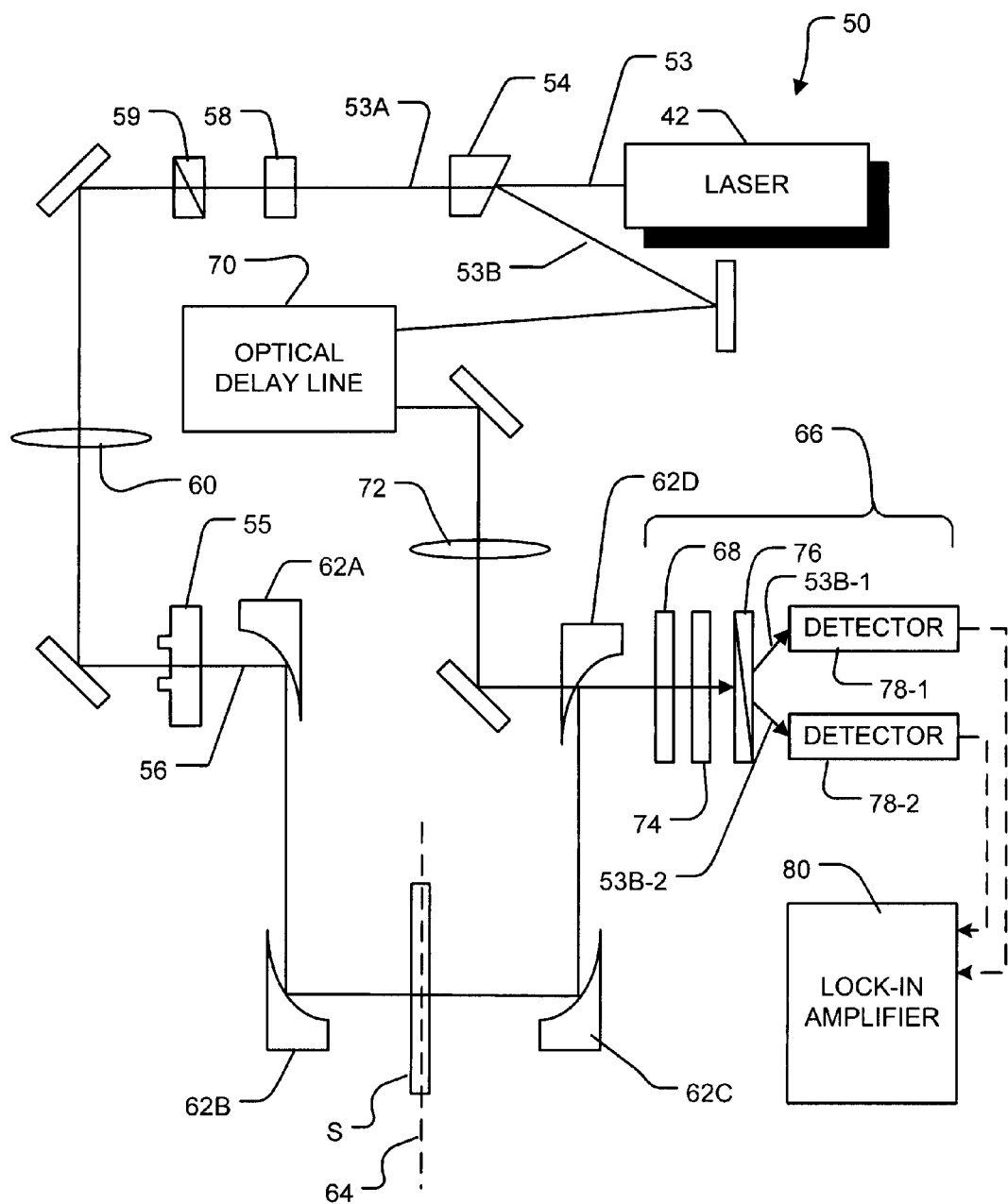

FIG. 7 shows another apparatus 50 that can be used to directly determine the variation in signal transit time through a sample with angle. Apparatus 50 comprises a source 42 of far-infrared radiation. Source 42 may comprise, for example, a Ti-sapphire laser. A beam 53 of radiation is split by a beam-splitter 54 into a pump beam 53A and a probe beam 53B. Pump beam 53A is focused onto a semi-large aperture photo-conductive switch 55 to generate THz radiation in the manner described, for example, in G. Zhao et al. *Design and performance of THz emission and detection setup based on a semi-insulating GaAs emitter*, Rev. Sci. Inst. v. 73, pp. 1715-1719, 2002, or Zhang et al. U.S. Pat. No. 5,420,595 entitled Microwave Radiation Source.

In a prototype embodiment of the invention, source 42 comprises a Ti:Sapphire oscillator providing 300 mW of output power in 100 fs pulses delivered at 80 MHz. In the prototype, switch 55 comprised a Si—GaAs substrate having electrodes formed with silver and having a minimum separation of 470 μm. Switch 55 was biased with a 250V peak 40 kHz sine wave.

In the apparatus of FIG. 7, pump beam 53A passes through a half-wave plate 58 and a polarizer 59 before it is focused on switch 55 by lens 60. THz radiation 56 is generated at switch 55. Parabolic mirrors 62A and 62B direct THz radiation 56 from switch 55 onto an intermediate focal plane 64 on which a sample S can be located. Parabolic mirrors 62C and 62D direct radiation 56 arriving from focal plane 64 onto a detector 66.

Probe beam 53B passes through an optical delay line 70 and is focused onto detector 66 by a lens 72.

In the prototype embodiment, detector 66 comprises a ZnTe crystal 68 that detects incident radiation by way of the linear electro-optic effect. The THz radiation from switch 55 interacts with probe beam 53B at crystal 68. Probe beam 53B initially has a known polarization, for example, it may be linearly horizontally polarized. The electric fields of the THz radiation alter the polarization of the probe beam. After interacting with the THz radiation at crystal 68, radiation from the probe beam passes through a quarter-wave plate 74 to a Wollaston prism 76.

Wollaston prism 76 splits the light from probe beam 53B into beams 53B-1 and 53B-2 that have mutually perpendicular polarization vectors. Beams 53B-1 and 53B-2 are respectively detected by light detectors 78-1 and 78-2. Light detectors 78-1 and 78-2 may be matched photodiodes, for example. The outputs from light detectors 78-1 and 78-2 are provided as inputs to a lock-in amplifier 80.

When THz radiation 56 changes the polarization of probe beam 53B, the balance between beams 53B-1 and 53B-2 is altered and the output of lock-in amplifier 80 changes.

Since the duration of each pulse of light in probe beam 53B is much shorter than the period of THz radiation 56, the way in which THz radiation 56 varies in time can be determined by sweeping optical delay line 70 to provide delays of different lengths. Optical delay line 70 may be computer-controlled to facilitate this. The output of lock-in amplifier 80 as a function of the setting of optical delay-line 70 provides a trace that indicates the time-variation of THz radiation 56.

Figure 8:
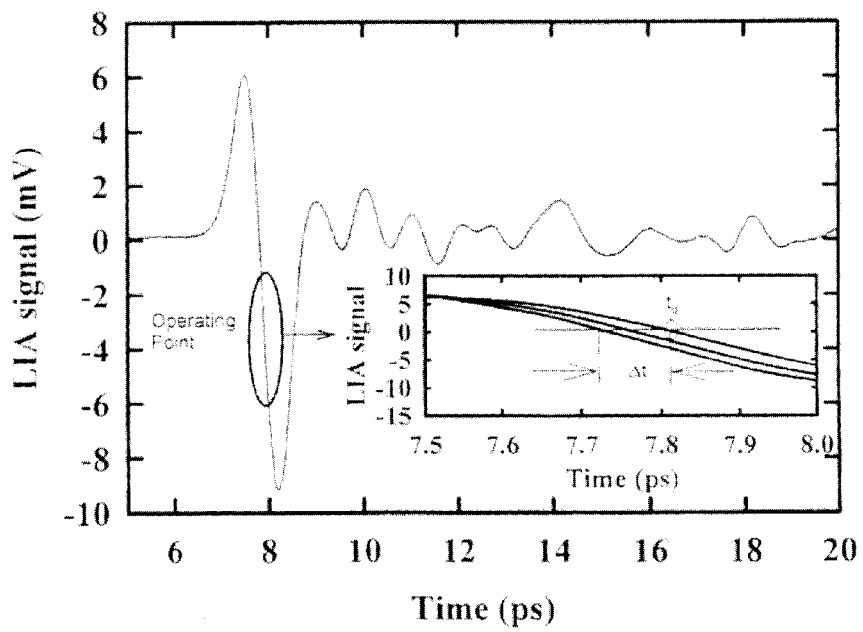
FIG. 8 shows the time evolution of a THz waveform and indicates a possible operating point for the apparatus of FIG. 7.

As noted above, the degree of anisotropy of fibers in a sample can be determined by monitoring the degree to which the sample delays the propagation of THz signal 56 for different relative angles between the polarization axis of signal 56 and the sample. The variation in this time delay can be conveniently measured in relation to a portion of the waveform of THz signal 56 that is rapidly varying. For example, where signal 56 exhibits a time variation as shown in the waveform 82 of FIG. 8, an operating point 84 may be selected on steeply-varying portion 86. Operating point 84 corresponds to a selected output level of lock-in amplifier 80.

As the sample is rotated relative to the polarization axis of signal 56, it is not necessary to scan optical delay line 70 to obtain a full time-domain waveform. It is only necessary to identify the delay that corresponds to the point on the waveform where the output signal from lock-in amplifier is at the operating point.

The way in which the delay at the operating point varies as the angle of the sample is changed provides information regarding anisotropies in the arrangements of fibers within the sample. The delay can be measured for several different angles. Preferably, the delay is determined for a selection of angles that spans approximately 90 degrees of rotation. In some embodiments, the selection of angles includes, for example, 4 to 15 different angles that span approximately 90 degrees.

The rate at which delays can be determined using the apparatus of FIG. 7 is limited by the time constant of the lock-in amplifier. In a prototype apparatus a lock-in time constant of 100 μs was used. This time constant permits an angular range of 90 degrees to be scanned at a sufficient number of angles to obtain a good indication of the degree of anisotropy of the fibers within a sample in significantly less than one second.

Figure 7A:
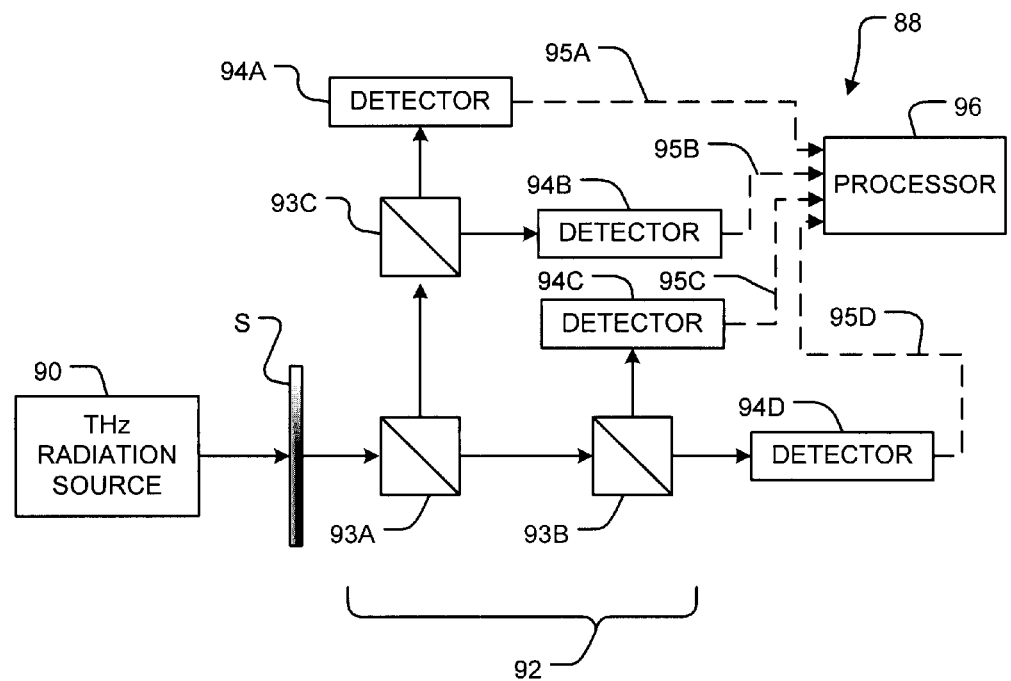

FIG. 7A is a schematic view of an alternative apparatus 88 useful for determining the degree of anisotropy of the fibers within a sample by making direct measurements of variations in the propagation times of THz radiation through the sample. Apparatus 88 has a source 90 of THz radiation that is directed to pass through a sample S. Source 90 can be controlled to selectively generate THz radiation of any of four polarization different states. The four polarization states may be linear polarization states although this is not mandatory. It is convenient for the four polarization states to include first and second pairs of orthogonal polarization states. For example, in some embodiments, the four polarization states include first and second pairs of orthogonal linear polarization states. In the example described in detail herein the four polarization states are linear polarization states identified as L1, L2, L3 and L4 with L1 horizontally polarized, L2 vertically polarized, L3 polarized at 45° above the horizontal and L4 polarized at 45° below the horizontal. This is a convenient choice for the four polarization states.

Apparatus 88 has a mechanism 92 that divides radiation that passes through sample S into 4 equal parts. In the illustrated embodiment, mechanism 92 comprises three non-polarizing beam splitters 93A, 93B, and 93C. Each of the four parts of radiation is detected at a coherent THz detector 94 (the detectors are identified individually as 94A, 94B, 94C and 94D). Associated with each detector 94 is a mechanism that permits determination of a time delay caused by the presence of sample S. This mechanism may be, for example, the mechanism illustrated in detail in FIG. 7.

Source 90 is controlled to generate THz radiation of each of the plurality of polarization states during a corresponding time interval with L1 being generated in a time interval t1, L2 being generated in a time interval t2, L3 being generated in a time interval t3 and L4 being generated in a time interval 14. Detectors 94 are gated so that detector 94A is active during t1, detector 94B is active during t2, detector 94C is active during t3, and detector 94D is active during t4. For each detector 94, an operating point is chosen on a portion of the corresponding THz waveform that is rapidly varying in the absence of a sample. Any deviations in time delay caused by the presence of sample S are manifested as changes in the amplitude of the signal detected at the detector 94 as described in the discussion of FIG. 7. Detectors 94 are zeroed in the absence of sample S (equivalently the outputs of detectors 94 are measured in the absence of sample S and the measured values are saved for use in determining the effect of sample S on the output signal).

Apparatus 88 may be operated to obtain information about the bulk average angle of fiber orientation in sample S and the degree of anisotropy in the arrangement of fibers within sample S by obtaining measurements 95 (identified individually as 95A, 95B, 95C and 95D) corresponding to each of detectors 94 during the time interval when the corresponding detector is active. The information may be obtained by processing measurements 95 in a processor 96.

A first value m1 may be obtained by subtracting measurements 95A and 95B for the first pair of orthogonal polarization states. A second value m2 may be obtained by subtracting measurements 95C and 95D for the second pair of orthogonal polarization states. Values indicating the degree of anisotropy of the fibers within sample S and the angle made by the preferred fiber orientation (if there is one) can be obtained from m1 and m2.

It can be seen that the absolute time delay $\Delta\tau$ caused by sample S on a THz pulse is given by:

$$\Delta\tau = \frac{L}{c}(n_\perp \cos(\theta) + n_\parallel \sin(\theta)) \tag{13}$$

where: L is the thickness of sample S, c is the speed of light in a vacuum, $\theta$ is the angle between the preferred axis of sample S and the angle of polarization of the THz radiation and $n_\perp$ and $n_\parallel$ are the indices of refraction for the birefringent sample S. It can be seen that:

$$m1 \propto \Delta n(\sin\theta + \cos\theta) \tag{14}$$

where $\Delta n = n_\perp - n_\parallel$.

For the particular example being described herein, where the polarization states are linear polarizations and the second pair of orthogonal polarization states are rotated by 45 degrees relative to the first pair of polarization states, it can be shown that:

$$\theta = \cot^{-1}\left(1 - \sqrt{2}\,\frac{m1}{m2}\right) \tag{15}$$

and $$\Delta n = \frac{\beta(m2)}{\sqrt{2}} \times \frac{1}{\sin\left(\cot^{-1}\left(1 - \sqrt{2}\,\frac{m1}{m2}\right)\right)} \tag{16}$$

where: $\beta$ is a constant calibration factor.

Figure 9:
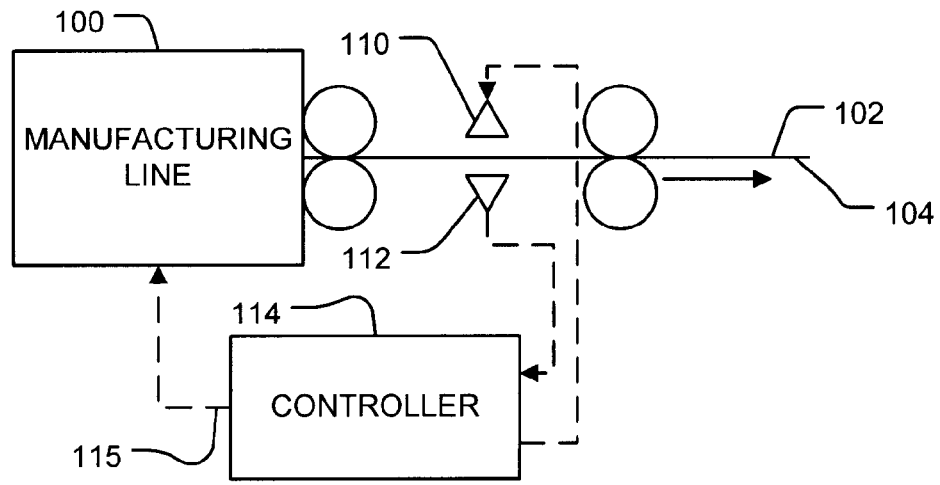
FIG. 9 shows schematically a plant for making a composite fibrous material that includes apparatus for evaluating the anisotropy of fibers in the fibrous material.

Any of the embodiments described above may be used to monitor the fiber arrangements during the manufacture of products such as OSB, particle board, papers or the like. FIG. 9 shows schematically an example application. In FIG. 9, a moving web 102 of a material 104 emerges from a manufacturing line 100. Material 104 is a fibrous composite material (meaning that material 104 is made by bonding together pieces of one or more starting materials and that material 104 includes fibers of some kind). Material 104 may be, for example, a composite wood product, for example, particle board, press board or OSB, a cardboard, or paper.

A source 110 of polarized THz radiation is located on a first side of web 102 and a detector 112 of the polarized THz radiation is located on a second side of web 102. The THz radiation is polarized along a polarization axis that is substantially in the plane of web 102. Source 110 and detector 112 are arranged so that the angle made by the polarization axis of the THz radiation to the direction of motion of web 102 can be varied through a range large enough to provide information regarding the degree of anisotropy in the arrangement of fibers within web 102.

Source 110 and detector 112 operate to obtain a measure of how the propagation speed of THz signals through web 102 varies with angle. Source 110 and detector 112 could, for example, be the source and detector in a system as shown in any one of FIGS. 1, 6, 6A, 7 or 7A. Apparatus for quality control in the manufacture of a composite fibrous material may comprise a controller connected to control the angle of polarization of the radiation emitted by the source.

The controller may comprise a data processor connected to receive output signals from detector 112 and to control the operation of source 110 and detector 112. For example, the controller may comprise a suitable industrial programmable controller, a programmed personal computer equipped with interfaces that allow it to read data from detector 112 and to write control signals to source 110 and detector 112 or the like. The controller is configured to operate the detector to obtain a measure of the degree of birefringence of the sample at THz wavelengths. This may be done directly by measuring a propagation speed of THz radiation in the material for each of a plurality of angles or indirectly, for example, by monitoring changes caused by the sample in the polarization states of two or more THz signals.

The controller may process the data from detector 110 to obtain information characterizing a distribution of fibers in the sample. A controller 114 is indicated schematically in FIG. 9. Similar controllers may be present in the apparatus shown in FIGS. 1, 6, 6A, 7 and 7A but are not shown in those Figures.

In some embodiments controller 114 may automatically control an orientation of fibers in one or more layers of the composite material and/or control a thickness of a layer of a component of the composite material in response to the processed information. The control may be maintained by delivering control signals 115 to manufacturing line 100. For those composite fibrous products in which it is desirable to have fibers distributed equally in orthogonal directions or for composite fibrous products in which it is desirable to have fibers randomly arranged with no bulk average preferred fiber orientation the controller may monitor deviations from zero birefringence and may optionally automatically control one or more process conditions to maintain the measured birefringence of the composite product to be zero or near to zero.

Figure 10A:
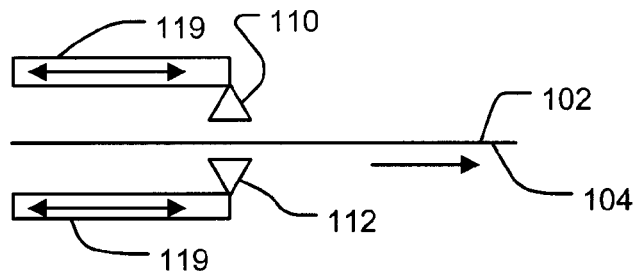
FIGS. 10A and 10B are schematic views of example mechanisms for measuring characteristics of the distributions of fibers at points within a moving web of material; and, FIG. 11 is a flow chart illustrating a method according to one example embodiment of the invention.

In some alternative embodiments, a THz radiation source and detector are mounted on an assembly that moves at, or approximately at, the speed of web 102 while measurements are being made so that variations in the propagation speed of the THz signals (or, equivalently, variations in the degree to which passage through the sample delays the THz signals) can be made at the same location on web 102 for a range of different polarization states while web 102 is moving. FIG. 10A shows an example embodiment wherein a source 110 and detector 112 are each mounted on a reciprocating shuttle 119.

Figure 10B:
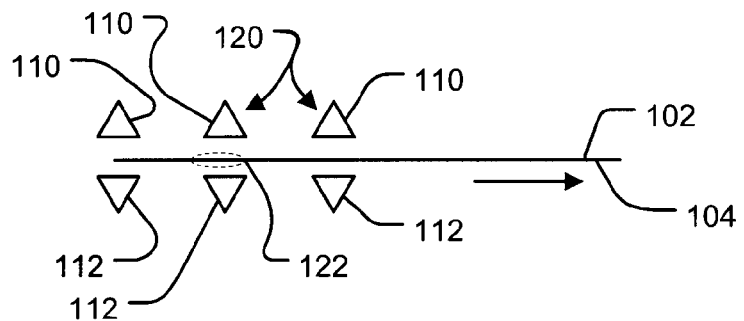

In some other alternative embodiments, two or more pairs 120 of source 110 and detector 112 are arranged at locations that are aligned with one another and spaced apart in a direction of motion of web 102. Different pairs 120 of source 110 and detector 112 are controlled to take measurements at times that coincide with a sample location 122 on web 102 being present adjacent the pair 120. Successive source-detector pairs 120 can measure propagation speed of THz radiation through the sample at the same sample location 122 for different polarization angles relative to web 102. An example of such an embodiment is shown schematically in FIG. 10B.

Figure 11:
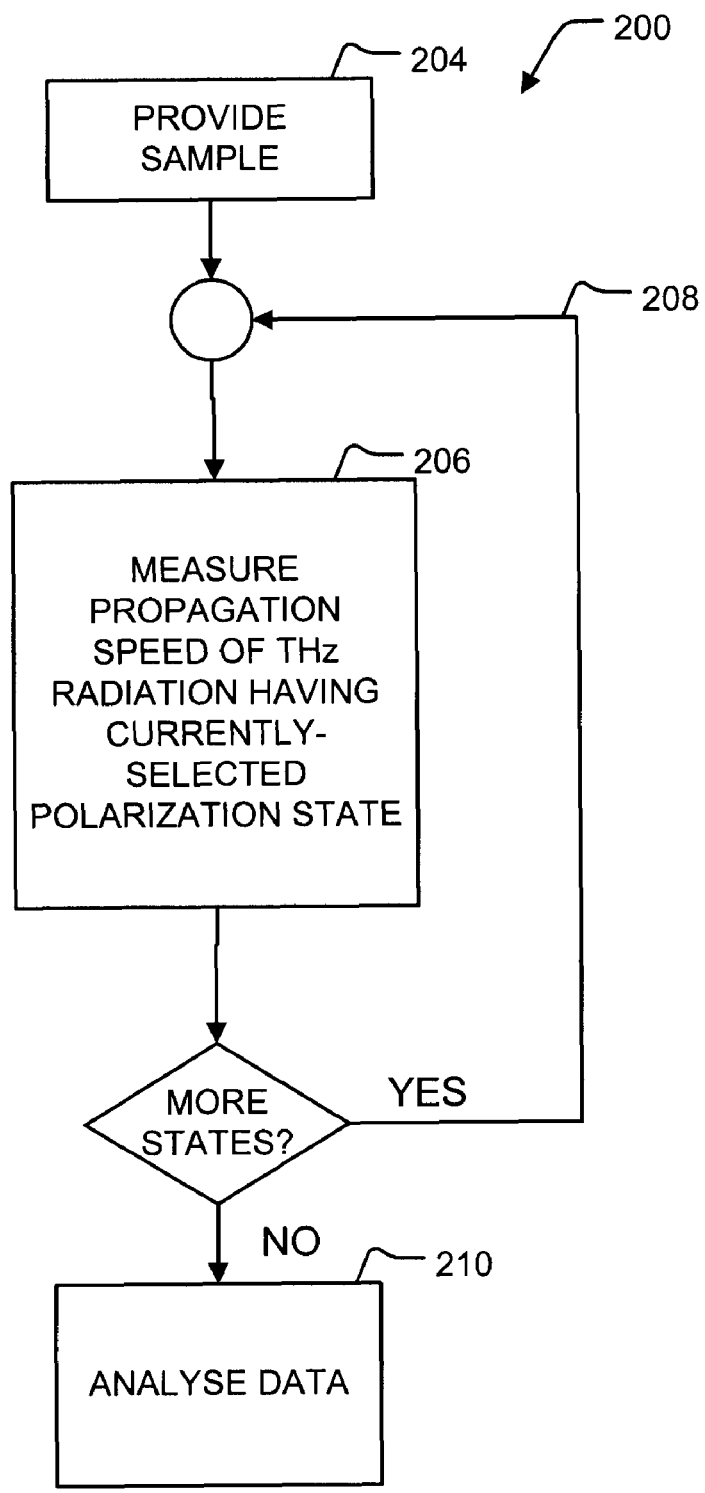

As described above, the arrangements of fibers in a sample of a composite product can be studied by observing how the speed of propagation of a polarized THz signal varies with the angle between the polarization axis of the signal and the sample. FIG. 11 is a flow chart illustrating a method 200 according to an example embodiment of the invention. The execution of method 200 may be coordinated by a programmed data processor. All calculations performed in method 200 may be executed automatically in a programmed data processor. Method 200 begins in block 204 by providing a sample of a composite product. The sample is preferably in the form of a sheet having substantially parallel faces. The composite product includes fibers that are distributed in some way in the plane of the sheet.

In block 206 method 200 obtains a measure of a speed of propagation of polarized THz radiation through the sheet for a given angle between a polarization axis of the THz radiation and an arbitrary reference direction in the plane of the sheet. The measure does not necessarily provide a numerical value for the speed. It is sufficient if the measure results in a value that varies as a function of the propagation speed of THz radiation through the sample.

Loop 208 indicates that block 206 is performed for a plurality of different polarization states (e.g. a plurality of different angles of the polarization axis of the THz radiation to the reference direction). For example, block 206 may be performed for a sequence of 4 to 25 angles. In some embodiments the angles are equally-spaced, for example by an angular step in the range of 1 to 13 degrees. The angles for which block 206 is performed preferably span at least 90 degrees. However, in some embodiments the angles span 45 degrees or even less.

In block 210 the data from block 206 is analyzed to detect patterns in the data. For example, the data from block 206 may be analyzed to obtain one or more of:
  a bulk volume-averaged fiber orientation;
  an angle between two axes along which fibers in the sample tend to be aligned;
  a relative amount of fibers in a sample which are generally aligned with each of two non-parallel axes in the sample;
  a measure of the degree to which fibers of the sample are arranged anisotropically in the plane of the sample; and/or
  the like.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for measuring average orientations of fibers in a composite fibrous material, the method comprising:
    passing first electromagnetic radiation through the material, the first electromagnetic radiation having a first polarization state and passing second electromagnetic radiation through the material, the second electromagnetic radiation having a second polarization state, the first and second electromagnetic radiation having one or more wavelengths at which the material is not opaque;

detecting the first and second electromagnetic radiation that has passed though the material; and, obtaining a measure of birefringence of a sample at the wavelengths of the electromagnetic radiation based at least in part on the detected first and second electromagnetic radiation.

2. A method according to claim 1 comprising measuring propagation speeds of the first and second electromagnetic radiation in the material.

3. A method according to claim 2 wherein measuring propagation speeds comprises measuring delays in the detection of the first and second electromagnetic radiation resulting from the presence of the sample.

4. A method according to claim 3 comprising detecting features of waveforms of the first and second electromagnetic radiation wherein measuring the propagation speeds of the electromagnetic radiation in the material comprises monitoring time intervals between reference times and times at which the features of the waveforms of the electromagnetic radiation are detected.

5. A method according to claim 4 wherein detecting the features of the waveforms comprises allowing each waveform to interact with a pulse of radiation in a probe beam and detecting a change in the probe beam caused by the feature of the waveform.

6. A method according to claim 5 comprising altering a point on the waveform that the pulse of radiation interacts with by passing the probe beam through an optical delay line and varying a delay provided by the optical delay line.

7. A method according to claim 2 wherein the first and second polarization states are linear polarization states wherein the first and second electromagnetic radiation are each polarized along a different polarization axis and wherein the polarization axes of the first and second electromagnetic radiation each make a different angle with a reference axis in the plane of the material.

8. A method according to claim 7 wherein the polarization axes of the first and second electromagnetic radiation are substantially parallel to a plane of the material.

9. A method according to claim 7 comprising monitoring a variation of the speed of propagation of the electromagnetic radiation as a function of the angle between the polarization axis of the electromagnetic radiation and the reference axis for 4 or more angles.

10. A method according to claim 9 wherein monitoring the variation of the speed of propagation of the electromagnetic radiation as a function of the angle comprises measuring the speed of propagation of the electromagnetic radiation in the material for a set of angles between the polarization axis of the electromagnetic radiation and the reference axis wherein the angles are separated from one another by 15 degrees or less and collectively span at least 80 degrees.

11. A method according to claim 7 wherein monitoring the variation of the speed of propagation of the electromagnetic radiation as a function of the angle is performed for a range of angles spanning at least 80 degrees.

12. A method according to claim 1 comprising measuring changes in the polarization states of the first and second electromagnetic radiation and obtaining the measure of birefringence based at least in part on the changes in the polarization states of the first and second electromagnetic radiation.

13. A method according to claim 12 wherein the first and second polarization states are not orthogonal to one another.

14. A method according to claim 12 wherein the first and second polarization states are linear polarization states wherein the first and second electromagnetic radiation are each polarized along a different polarization axis and wherein the polarization axes of the first and second electromagnetic radiation each make a different angle with a reference axis in the plane of the material.

15. A method according to claim 14 wherein the polarization axes of the first and second electromagnetic radiation are substantially parallel to a plane of the material.

16. A method according to claim 1 wherein the electromagnetic radiation is THz radiation.

17. A method according to claim 16 wherein the one or more wavelengths are in the range of 0.01 THz to 1.5 THz.

18. A method according to claim 16 wherein the THz radiation has a broad band spectrum that extends from at least about 0.2 THz to about 0.9 THz.

19. A method according to claim 1 wherein the fibers comprise cellulose fibers.

20. A method according to claim 19 wherein the material comprises a material selected from: pieces of wood; oriented strand board; and particle board.

21. A method according to claim 1 wherein the fibers comprise carbon fibers.

22. A method according to claim 1 wherein the material forms a web of material moving in a plane of the material and the method is performed while the material is moving.

23. A method according to claim 22 wherein passing the electromagnetic radiation through the material comprises passing the electromagnetic radiation from a source to a detector and the method comprises moving the source and detector to follow a location on the web of material.

24. A method according to claim 1 comprising computing a bulk average fiber orientation at a location in the material based at least in part on the detected first and second electromagnetic radiation.

25. Apparatus for quality control in the manufacture of a composite fibrous material, the apparatus comprising:

a source of THz radiation located to direct polarized THz radiation at a first face of a moving web of the composite fibrous material with a selected one of a plurality of polarization states;

a detector of THz radiation located to receive the THz radiation originating from the source and emerging on a second face of the composite fibrous material; and, a controller connected to select a polarization state of the source and configured to operate the detector and obtain a measure of birefringence of the material at wavelengths of the THz radiation.

26. Apparatus according to claim 25 wherein the plurality of polarization states comprise linear polarization states and the controller is connected to set an axis of polarization of the THz radiation to have a desired angle relative to a direction of motion of the web.

* * * * *